US011666309B2

(12) United States Patent
Zelenka

(10) Patent No.: US 11,666,309 B2
(45) Date of Patent: Jun. 6, 2023

(54) CATHETER SHEATH SYSTEM AND METHOD

(71) Applicant: ACIST Medical Systems, Inc., Eden Prairie, MN (US)

(72) Inventor: Robert Zelenka, Milpitas, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 1067 days.

(21) Appl. No.: 14/575,085

(22) Filed: Dec. 18, 2014

(65) Prior Publication Data

US 2015/0173710 A1 Jun. 25, 2015

Related U.S. Application Data

(60) Provisional application No. 61/918,361, filed on Dec. 19, 2013.

(51) Int. Cl.
| | |
|---|---|
| *A61B 8/00* | (2006.01) |
| *A61B 8/12* | (2006.01) |
| *A61L 29/08* | (2006.01) |
| *A61L 31/04* | (2006.01) |
| *A61L 29/04* | (2006.01) |
| *A61L 29/14* | (2006.01) |
| *A61L 31/10* | (2006.01) |
| *A61L 31/14* | (2006.01) |

(52) U.S. Cl.
CPC ............ *A61B 8/445* (2013.01); *A61B 8/12* (2013.01); *A61L 29/041* (2013.01); *A61L 29/048* (2013.01); *A61L 29/085* (2013.01); *A61L 29/14* (2013.01); *A61L 31/048* (2013.01); *A61L 31/10* (2013.01); *A61L 31/14* (2013.01)

(58) Field of Classification Search
CPC ......... A61B 8/12; A61B 8/445; A61L 29/085; A61L 31/048; A61L 29/048; A61L 29/14; A61L 29/041; A61L 31/10; A61L 31/14
See application file for complete search history.

(56) References Cited

U.S. PATENT DOCUMENTS

| | | | |
|---|---|---|---|
| 4,582,181 | A | 4/1986 | Samson |
| 4,636,346 | A | 1/1987 | Gold et al. |
| 4,728,694 | A | 3/1988 | Batich et al. |
| | | (Continued) | |

FOREIGN PATENT DOCUMENTS

| | | |
|---|---|---|
| CN | 1810213 A | 8/2006 |
| CN | 203196120 U | 9/2013 |
| | (Continued) | |

OTHER PUBLICATIONS

Giants, "Crystallinity and Dielectric Properties of PEEK, Poly (ether ether ketone)," Abstract, IEEE Transactions on Dielectrics and Electrical Insulation, vol. 1, No. 6, 1994.

(Continued)

*Primary Examiner* — Jason M Ip
*Assistant Examiner* — Renee C Langhals
(74) *Attorney, Agent, or Firm* — Fredrikson & Byron, P.A.

(57) ABSTRACT

A catheter is disclosed comprising a sheath surrounding an inner lumen. The inner lumen is configured to receive a fluid. The sheath includes a sheath portion that comprises a hydrophilic material, wherein the hydrophilic material is in direct contact with the fluid. The hydrophilic material helps resist formation of air bubbles along the inner lumen.

15 Claims, 3 Drawing Sheets

(56) References Cited

U.S. PATENT DOCUMENTS

| | | | |
|---|---|---|---|
| 4,870,887 A | 10/1989 | Tresslar et al. | |
| 4,976,690 A | 12/1990 | Solar et al. | |
| 5,037,404 A | 8/1991 | Gold et al. | |
| 5,201,316 A | 4/1993 | Pomeranz et al. | |
| 5,240,985 A * | 8/1993 | Gardiner | C08L 23/02 524/274 |
| 5,250,069 A | 10/1993 | Nobuyoshi et al. | |
| 5,312,356 A | 5/1994 | Engelson et al. | |
| 5,316,706 A | 5/1994 | Muni et al. | |
| 5,330,444 A | 7/1994 | Webler et al. | |
| 5,399,164 A | 3/1995 | Snoke et al. | |
| 5,400,785 A * | 3/1995 | Crowley | A61B 8/12 600/467 |
| 5,443,457 A | 8/1995 | Ginn et al. | |
| 5,531,721 A | 7/1996 | Pepin et al. | |
| 5,538,512 A | 7/1996 | Zenzen et al. | |
| 5,542,924 A | 8/1996 | Snoke et al. | |
| 5,584,821 A | 12/1996 | Hobbs et al. | |
| 5,624,397 A | 4/1997 | Snoke et al. | |
| 5,715,825 A | 2/1998 | Crowley | |
| 5,720,300 A | 2/1998 | Fagan et al. | |
| 5,738,100 A | 4/1998 | Yagami et al. | |
| 5,762,066 A | 6/1998 | Law et al. | |
| 5,824,030 A | 10/1998 | Yang et al. | |
| 5,851,203 A | 12/1998 | van Muiden | |
| 5,951,480 A * | 9/1999 | White | A61B 8/12 600/463 |
| 5,957,910 A | 9/1999 | Holden et al. | |
| 6,007,478 A | 12/1999 | Siess et al. | |
| 6,126,650 A | 10/2000 | Martinez et al. | |
| 6,159,228 A | 12/2000 | Frid et al. | |
| 6,180,059 B1 * | 1/2001 | Divino, Jr. | A61M 1/1698 422/44 |
| 6,264,633 B1 | 7/2001 | Knorig | |
| 6,454,997 B1 * | 9/2002 | Divino, Jr. | A61M 1/3621 128/DIG. 3 |
| 6,524,303 B1 | 2/2003 | Garibaldi | |
| 6,610,068 B1 | 8/2003 | Yang | |
| 6,648,024 B2 | 11/2003 | Wang | |
| 6,676,900 B1 * | 1/2004 | Divino, Jr. | A61M 1/1698 261/DIG. 28 |
| 6,712,766 B2 | 3/2004 | Harada | |
| 6,929,635 B2 | 8/2005 | Shelso | |
| 7,387,826 B2 | 6/2008 | Burgmeier et al. | |
| 7,632,236 B2 | 12/2009 | Kaneto et al. | |
| 2002/0022825 A1 | 2/2002 | Saitou et al. | |
| 2002/0188189 A1 | 12/2002 | Belef et al. | |
| 2003/0195490 A1 | 10/2003 | Boatman et al. | |
| 2003/0236495 A1 | 12/2003 | Kennedy | |
| 2004/0073158 A1 | 4/2004 | Shah | |
| 2005/0090852 A1 | 4/2005 | Layne et al. | |
| 2005/0101859 A1 | 5/2005 | Maschke | |
| 2005/0125002 A1 | 6/2005 | Baran et al. | |
| 2005/0142314 A1 | 6/2005 | Burgmeier et al. | |
| 2005/0154442 A1 * | 7/2005 | Eidenschink | A61F 2/856 623/1.11 |
| 2005/0203396 A1 | 9/2005 | Angelsen et al. | |
| 2005/0261586 A1 | 11/2005 | Makin et al. | |
| 2006/0084964 A1 | 4/2006 | Knudson et al. | |
| 2007/0134305 A1 * | 6/2007 | Zilberman | A61K 9/70 424/443 |
| 2007/0167824 A1 | 7/2007 | Lee et al. | |
| 2007/0240817 A1 | 10/2007 | Strong et al. | |
| 2007/0244501 A1 * | 10/2007 | Horn | A61L 29/085 606/194 |
| 2008/0109057 A1 | 5/2008 | Calabria et al. | |
| 2009/0081298 A1 * | 3/2009 | Murase | C07K 7/06 424/489 |
| 2009/0163818 A1 | 6/2009 | Zelenka et al. | |
| 2009/0270737 A1 | 10/2009 | Thornton | |
| 2009/0297582 A1 | 12/2009 | Meyer | |
| 2010/0063477 A1 | 3/2010 | Ohigawa | |
| 2010/0152590 A1 * | 6/2010 | Moore | A61B 8/12 600/466 |
| 2010/0185172 A1 | 7/2010 | Fabro | |
| 2010/0204605 A1 | 8/2010 | Blakley et al. | |
| 2011/0091515 A1 * | 4/2011 | Zilberman | A61L 27/54 424/409 |
| 2012/0252709 A1 * | 10/2012 | Felts | A61M 5/3129 508/100 |
| 2012/0277772 A1 * | 11/2012 | Aben | A61L 17/005 606/151 |
| 2012/0289837 A1 | 11/2012 | Zelenka | |
| 2013/0172872 A1 * | 7/2013 | Subramaniam | A61B 18/00 606/33 |
| 2013/0253328 A1 | 9/2013 | Zelenka et al. | |
| 2014/0187964 A1 * | 7/2014 | Corl | B06B 1/0622 600/467 |
| 2014/0276756 A1 * | 9/2014 | Hill | A61B 18/1492 606/33 |
| 2015/0272732 A1 * | 10/2015 | Tilson | A61M 25/1002 623/2.11 |
| 2016/0022244 A1 * | 1/2016 | Courtney | A61B 8/445 600/466 |
| 2017/0071710 A1 | 3/2017 | Deturmeny | |

FOREIGN PATENT DOCUMENTS

| | | |
|---|---|---|
| EP | 1955724 A1 | 8/2008 |
| JP | H05-084247 A | 4/1993 |
| JP | H08-57035 A | 3/1996 |
| JP | H08-140976 A | 6/1996 |
| JP | H08-275947 A | 10/1996 |
| JP | 2000152940 A | 6/2000 |
| JP | 2002109217 A | 4/2002 |
| JP | 2002528188 A | 9/2002 |
| JP | 2003126092 A | 5/2003 |
| JP | 2003210462 A | 7/2003 |
| JP | 3571939 B2 | 9/2004 |
| JP | 2005006776 A * | 1/2005 |
| JP | 2005006776 A | 1/2005 |
| JP | 2005013453 A | 1/2005 |
| JP | 2005052667 A | 3/2005 |
| JP | 2006075611 A | 3/2006 |
| JP | 2007152101 A | 6/2007 |
| JP | 2012024491 A | 2/2012 |
| WO | 9221965 A1 | 12/1992 |
| WO | 9414494 A2 | 7/1994 |
| WO | 9714466 A1 | 4/1997 |
| WO | 9850098 A1 | 11/1998 |
| WO | 0033742 A2 | 6/2000 |
| WO | 02053632 A2 | 7/2002 |
| WO | 2009134171 A1 | 11/2009 |
| WO | 2011027821 A1 | 3/2011 |
| WO | 2013142649 A1 | 9/2013 |

OTHER PUBLICATIONS

Kurtz et al., "PEEK Biomaterials in Trauma, Orthopedic, and Spinal Implants," Biomaterials, vol. 28, No. 32, 2007, pp. 4845-4869.

U.S. Appl. No. 61/484,941, entitled "Variable-Stiffness Imaging Window and Production Method Thereof," filed May 11, 2011, 19 pages.

Notification of Transmittal of the International Search Report and the Written Opinion of the International Searching Authority, or the Declaration for co-pending Intl. Pat. App. No. PCT/US2014/071268 dated Mar. 23, 2015, 12 pages, European Patent Office, Rijswijk, The Netherlands.

English Abstract and Machine Translation for Japanese Publication No. 2005-006776 A, published Jan. 13, 2005, 9 pgs.

Office Action and English Translation dated Jun. 21, 2021 from related Chinese Application No. 201480063687.1, 16 pgs.

* cited by examiner

CATHETER SHEATH SYSTEM AND METHOD

FIELD

This application claims the benefit of U.S. Provisional Application Ser. No. 61/918,361 filed Dec. 19, 2013, the contents of which are hereby incorporated by reference.

BACKGROUND

Catheters are used to access patients and diagnose and treat diseases. They are typically used in medical practice to reach locations inside the body otherwise unreachable without surgery. For example, patients suffering from coronary artery disease may receive percutaneous coronary interventions for treatment of the disease. An intravascular catheter may be used to evaluate the coronary artery disease as well as guide the selection of treatment devices. Catheters typically have a long and tubular sheath that defines an inner lumen. Catheters also have a distal end which enters the patient as well as a proximal end that is controlled by a system user.

The catheter sheath defines an inner lumen through which a medical device can be inserted during a medical procedure. Often times, as the medical device inserts into and moves through the inner lumen, air or gas bubbles form within the inner lumen. These bubbles can cause a variety of problems. As such, system users often insert fluid into the sheath in order to flush out these bubbles. However, flushing is time consuming. Also, in some cases, bubbles can remain trapped even after flushing is performed.

In some medical procedures, catheters are used as a part of an intra-vascular ultrasound (IVUS) system. A standard IVUS system includes a control module, an imaging catheter and a transducer positioned within an inner lumen of the catheter. As the transducer moves through the inner lumen, the transducer produces images of the inside walls of the blood vessel. However, bubbles trapped within the inner lumen can interfere with the IVUS system and cause problems with ultrasound image quality.

It would be advantageous to provide a catheter that resists air or gas bubble formation. It would also be advantageous to provide a catheter that allows for easier flushing of bubbles. It would further be advantageous to provide an imaging catheter and IVUS system that has enhanced image quality.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives. For example, each time the term "comprising" is used, in alternative embodiments, "comprising" can be replaced with "consisting essentially of" or "consisting of."

Figure 1:
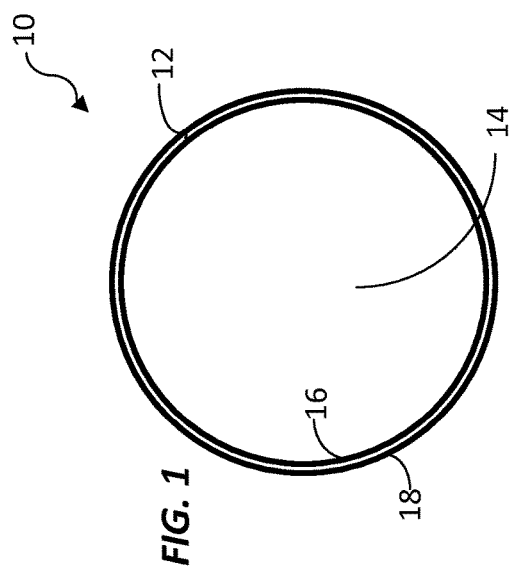
FIG. 1 is cross-sectional front view of a catheter according to an embodiment.

FIG. 1 is a cross-sectional front view of a catheter 10 according to an embodiment. The catheter 10 includes a sheath 12 surrounding an inner lumen 14. The inner lumen 14 is configured to receive a fluid. The inner lumen 14 also has a size through which a medical device can be slidably inserted during a medical procedure. As such, the sheath inner lumen 14 includes a diameter larger than the diameter of the medical device.

The sheath 12 also includes an inner surface 16 and an outer surface 18. The inner surface 16 defines the inner lumen 14 and is in contact with the fluid within the inner lumen 14. As a medical device inserts into and moves through the sheath 12, air bubbles can form along the inner surface 16 of the inner lumen 14. Operators commonly insert fluid into the inner lumen 14 in order to flush these air bubbles out. However, flushing is time consuming and often times, air bubbles remain trapped along the inner surface 16 even after flushing.

The present catheter 10 includes a sheath portion 24 that comprises a hydrophilic material that is in direct contact with the fluid in the inner lumen 14. The hydrophilic material in the sheath portion 24 helps reduce the number of air bubbles trapped along the inner surface 16 of the inner lumen 14. The hydrophilic material also helps to dislodge trapped air bubbles. In some cases, the sheath portion 24 has an inner surface 16 that includes hydrophilic material that is in direct contact with the fluid. In other cases, the entire sheath portion 24, including the inner surface 16 and the outer surface 18, includes hydrophilic material.

Figure 2:
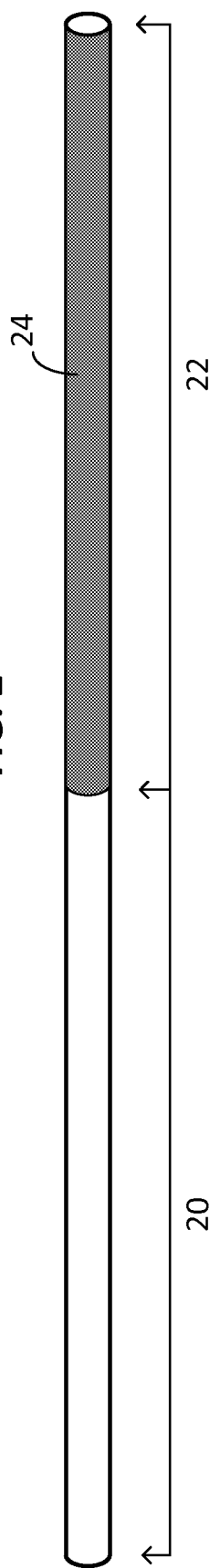
FIG. 2 is a side view of a catheter having a sheath portion according to an embodiment.
Figure 3:
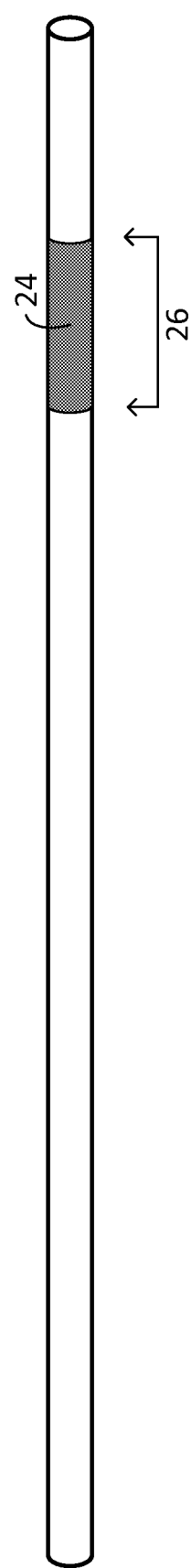
FIG. 3 is a side view of a catheter having a sheath portion according to another embodiment.
Figure 4:
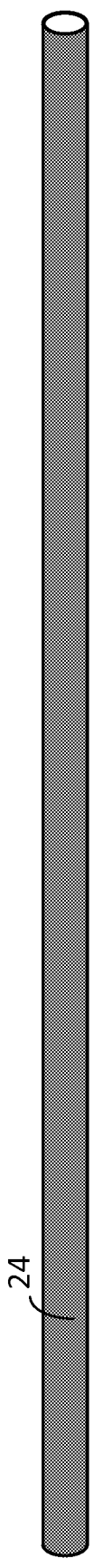
FIG. 4 is a side view of a catheter having a sheath portion according to another embodiment.

The sheath portion 24 that includes the hydrophilic material can be located at a desired location on the catheter 10. FIGS. 2-4 illustrate different embodiments of the sheath portion 24. Referring to FIG. 2, the catheter 10 includes a proximal end 20 and a distal end 22. The proximal end 20 is the catheter portion that generally remains outside of the patient's body. The distal end 22 is the catheter portion that can be inserted into a patient's body.

In some embodiments, the sheath portion 24 is located on the distal end 22 of the catheter 10. In some cases, the sheath portion 24 is the entire distal end 22, as shown in FIG. 2. In other cases, as shown in FIG. 3, the sheath portion 24 is an imaging window 26 located on the distal end 22. In other embodiments, as shown in FIG. 4, the sheath portion 24 is the entire catheter 10. Here, the entire catheter 10 comprises a hydrophilic material that is in direct contact with fluid inside the inner lumen 14.

The hydrophilic material can be any hydrophilic material that is substantially transparent to ultrasound energy. In some cases, the hydrophilic material comprises an amphiphile. The inclusion of a hydrophilic material increases the surface energy of the sheath portion 24. In some cases, the sheath portion 24 has a surface energy of at least about 35 dynes, at least about 40 dynes, at least about 45 dynes or at least about 50 dynes. In other cases, the sheath portion 24 has a surface energy that is greater than or equal to the surface energy of fluid in the inner lumen 14. In certain cases, the inner lumen receives saline solution as the fluid and the sheath portion has a surface energy of greater than or equal to the surface energy of saline solution.

In some embodiments, the sheath portion 24 includes both a biocompatible material and a hydrophilic material. The biocompatible materials can be materials such as nylon, polyurethane and polyethylene. In some cases, the sheath portion 24 includes both a polyethylene and a hydrophilic material. In certain cases, the sheath portion 24 is a hydrophilic polyethylene material disclosed in U.S. Pat. Nos. 4,728,694, 5,240,985, or WO2002053632, the entire contents of each which are incorporated herein by reference.

Figure 5:
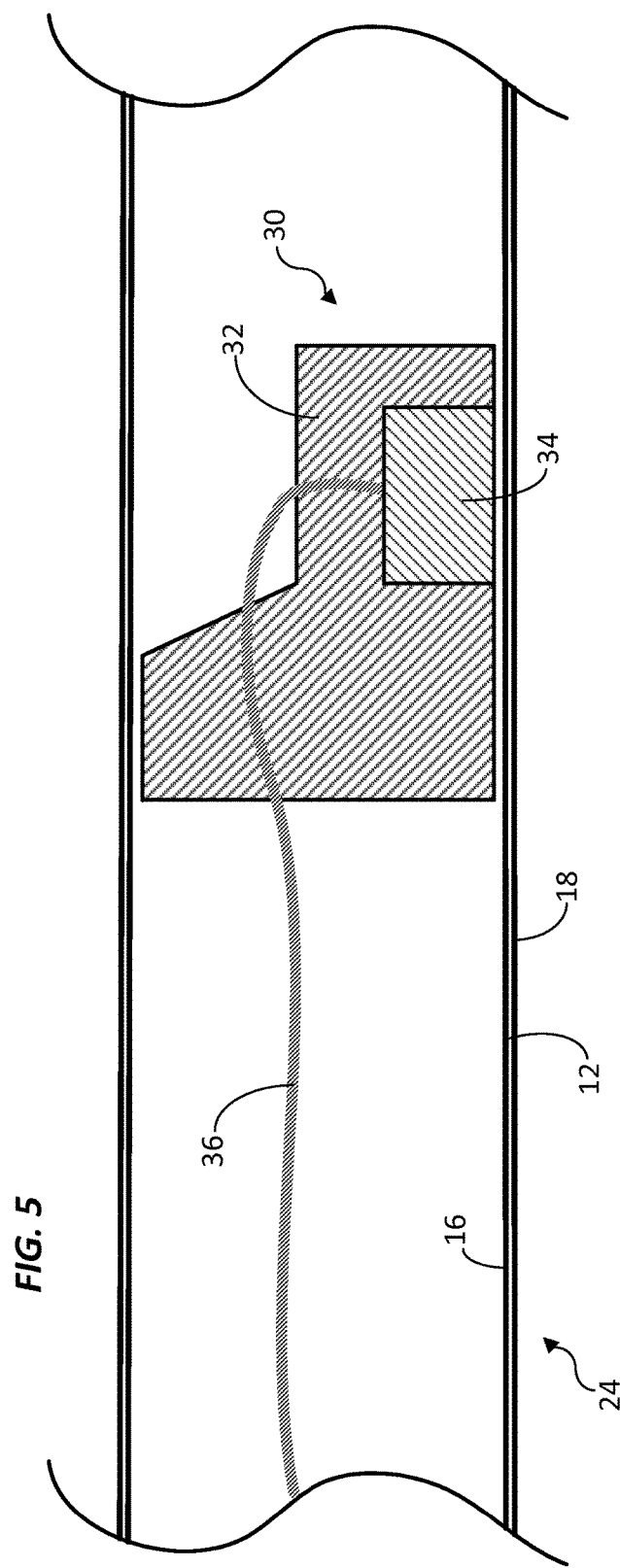
FIG. 5 is cross-sectional side view of an imaging catheter and an imaging core within the imaging catheter according to an embodiment.

In some embodiments, the catheter 10 is an imaging catheter. In other cases, the catheter 10 is an ultrasound imaging catheter. In yet other cases, the catheter 10 is an IVUS imaging catheter. FIG. 5 is cross-sectional side view of a sheath portion 24 of an imaging catheter 10. The imaging catheter 10 is configured to receive an imaging core 30 within the inner lumen 14. The imaging core 30 includes a transducer housing 32 and an ultrasound transducer 34. The ultrasound transducer 34 is also electrically coupled to an electrical cable 36. The ultrasound transducer 34 is configured to emit and receive ultrasound energy and generate ultrasound data.

As the imaging core 30 moves through the inner lumen 14, the transducer 34 produces images of the inside walls of the blood vessel. However, the movement of the imaging core 30 through the inner lumen 14 can also generate air bubbles. However, since the sheath portion 24 comprises a hydrophilic material in contact with the fluid, the air bubbles resist formation along the inner lumen 14 and/or are more easily flushed with a flushing fluid.

Figure 6:
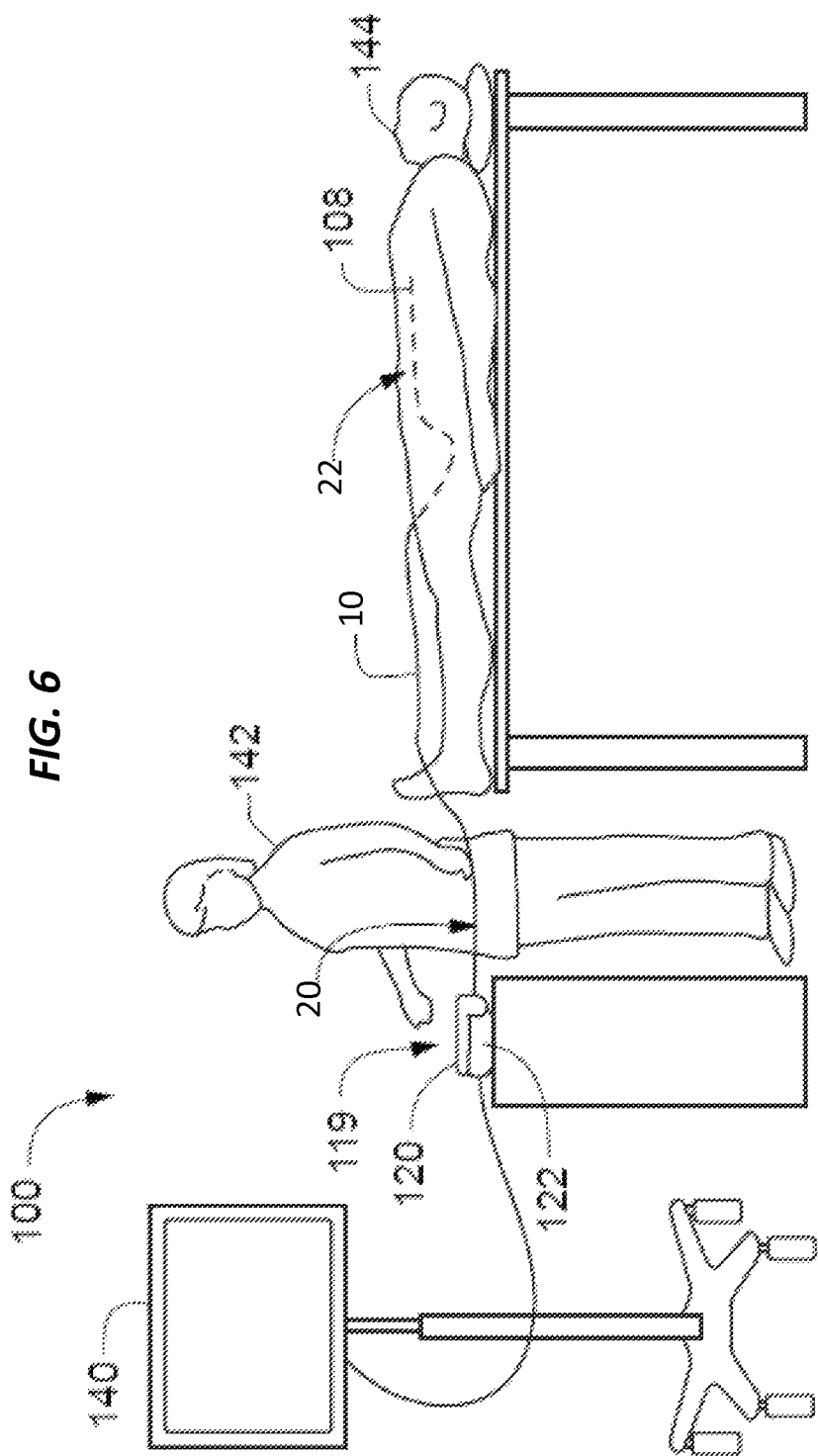
FIG. 6 is an illustrative example of an IVUS system configured to perform intravascular imaging.

In some embodiments, the catheter 10 is an IVUS imaging catheter that is part of an IVUS imaging system. FIG. 6 is an illustrative example of an IVUS system 100. The system 100 includes the catheter 10, a translation device 119, and a computing device 140. The catheter 102 includes a proximal end 20 and a distal end 22 configured to be inserted into a vessel of a patient 144. In one example, catheter 10 may be inserted into the patient 144 via the femoral artery and guided to an area of interest within the patient 144. The broken lines in FIG. 6 represent the distal end 22 of catheter 10 within the patient 144.

Some embodiments provide methods of manufacturing catheters having sheath portions 24 comprising a hydrophilic material. In some cases, a hydrophilic material can be added as a resin to a polymer extrusion that is used to manufacture a catheter sheath. Here, any known method of manufacturing a catheter can be used, wherein a hydrophilic material is added to the polymer extrusion.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

What is claimed is:

1. A catheter comprising:
a sheath surrounding an inner lumen, the inner lumen being configured to receive a fluid;
wherein the sheath includes a sheath portion, wherein the sheath portion comprises an ultrasonic imaging window that is transparent to ultrasound energy, the ultrasonic imaging window having an inner surface and an outer surface and a hydrophilic material that is transparent to ultrasound energy, wherein the hydrophilic material comprises an amphiphile that is transparent to ultrasound energy and the hydrophilic material is included at the ultrasonic imagining window form the inner surface to the outer surface of the ultrasonic imaging window and along a length of the ultrasonic imaging window, and wherein the hydrophillic material is configured to resist air bubbles forming along the inner surface as a result of image core movement within the inner lumen.

2. The catheter of claim 1 wherein the catheter is an imaging catheter.

3. The catheter of claim 1 wherein the sheath portion comprises a polyethylene material and a hydrophilic material.

4. The catheter of claim 1 wherein the sheath portion consists essentially of a polyethylene material and a hydrophilic material.

5. The catheter of claim 1 wherein the sheath has a distal end a proximal end, wherein the sheath portion is located on the distal end.

6. The catheter of claim 5 wherein the sheath portion is an entire distal end.

7. The catheter of claim 5 wherein the ultrasonic imaging window is located on the distal end.

8. The catheter of claim 1 wherein the sheath portion is the entire catheter.

9. The catheter of claim 1 wherein the sheath portion that includes the amphiphile that is transparent to ultrasound energy has a surface energy of at least 35 dynes.

10. The catheter of claim 1 wherein the sheath portion that includes the amphiphile that is transparent to ultrasound energy has a surface energy of at least 40 dynes.

11. The catheter of claim 1 wherein the sheath portion that includes the amphiphile that is transparent to ultrasound energy has a surface energy of at least 45 dynes.

12. The catheter of claim 1 wherein the sheath portion that includes the amphiphile that is transparent to ultrasound energy has a surface energy of 50 dynes.

13. The catheter of claim 1 wherein the fluid has a surface energy x and the sheath portion has a surface energy of greater than or equal to x.

14. A catheter comprising:
a sheath surrounding an inner lumen, the inner lumen being configured to receive a fluid;
wherein the sheath includes a sheath portion comprising an ultrasonic imaging window that is transparent to ultrasound energy, the ultrasonic imaging window having an inner surface and an outer surface and a hydrophilic material at a location that is configured to be in direct contact with the fluid, wherein the hydrophilic material comprises an amphiphile that is transparent to ultrasound energy, wherein the fluid has a surface energy x and the sheath portion that includes the amphiphile that is transparent to ultrasound energy has a surface energy of greater than or equal to x.

15. The catheter of claim 14, wherein the hydrophilic material is configured to resist air bubbles forming along the inner surface as a result of image core movement within the inner lumen.

\* \* \* \* \*